United States Patent
Bhowmik et al.

(10) Patent No.: US 9,833,012 B2
(45) Date of Patent: Dec. 5, 2017

(54) ENZYMATIC PROCESS

(71) Applicant: Givaudan SA, Vernier (CH)

(72) Inventors: Tarun Bhowmik, Mason, OH (US); Stefka Ivanova Myaka, Loveland, OH (US); Johan Peter Van Leersum, Morrow, OH (US); Roy Wade Smith, Cold Spring, KY (US)

(73) Assignee: GIVAUDAN S.A., Vernier (CH)

( * ) Notice: Subject to any disclaimer, the term of this patent is extended or adjusted under 35 U.S.C. 154(b) by 5 days.

(21) Appl. No.: 14/824,682

(22) Filed: Aug. 12, 2015

(65) Prior Publication Data

US 2015/0342236 A1 Dec. 3, 2015

Related U.S. Application Data

(63) Continuation of application No. 12/996,731, filed as application No. PCT/CH2009/000201 on Jun. 15, 2009, now abandoned.

(60) Provisional application No. 61/074,167, filed on Jun. 20, 2008.

(51) Int. Cl.
| | |
|---|---|
| A23L 1/237 | (2006.01) |
| A23L 1/23 | (2006.01) |
| A23J 3/34 | (2006.01) |
| A23L 27/00 | (2016.01) |
| A23L 27/24 | (2016.01) |
| A23L 27/40 | (2016.01) |

(52) U.S. Cl.
CPC ............. *A23L 1/2375* (2013.01); *A23J 3/346* (2013.01); *A23L 27/24* (2016.08); *A23L 27/40* (2016.08); *A23L 27/45* (2016.08); *A23L 27/88* (2016.08); *C12Y 302/01058* (2013.01); *C12Y 304/11* (2013.01); *C12Y 304/13* (2013.01); *C12Y 304/14* (2013.01); *C12Y 304/15* (2013.01); *C12Y 304/16* (2013.01); *C12Y 304/17* (2013.01); *C12Y 304/18* (2013.01); *C12Y 304/19* (2013.01); *C12Y 304/21* (2013.01); *C12Y 304/21062* (2013.01); *C12Y 304/22* (2013.01); *C12Y 304/23* (2013.01); *C12Y 304/24* (2013.01); *C12Y 304/25* (2013.01); *C12Y 305/01002* (2013.01); *A23V 2002/00* (2013.01)

(58) Field of Classification Search
CPC ................................. A23L 1/2375; A23L 1/23
USPC ........................................................... 426/52
See application file for complete search history.

(56) References Cited

U.S. PATENT DOCUMENTS

| | | | |
|---|---|---|---|
| 3,615,721 A | 10/1971 | Silberman | |
| 3,852,479 A | 12/1974 | Yokotsuka et al. | |
| 5,958,755 A | 9/1999 | Skelton et al. | |
| 6,024,990 A | 2/2000 | Kofoed et al. | |
| 6,514,941 B1 | 2/2003 | Tolton, II et al. | |
| 6,838,100 B2 * | 1/2005 | Jaeger ....................... | A23J 3/34 |
| | | | 426/42 |

FOREIGN PATENT DOCUMENTS

| | | |
|---|---|---|
| DE | 4226744 A1 | 11/1992 |
| DE | 10056067 A1 | 5/2002 |
| EP | 1163853 A1 | 12/2001 |
| GB | 1254950 A | 11/1971 |
| JP | H01309655 A | 12/1989 |
| WO | 9818342 A1 | 5/1998 |
| WO | 2005070220 A1 | 8/2005 |
| WO | 2005096847 A1 | 10/2005 |
| WO | 2007042274 A1 | 4/2007 |
| WO | 2008007672 A1 | 1/2008 |
| WO | 2008122138 A1 | 10/2008 |
| WO | 2009114954 A1 | 9/2009 |

OTHER PUBLICATIONS

JP-2006-075084—Machine Translation.*
De Iliev I, et al., "Protein Concentrates andHydrolysates form Spinach and Nettles", XP002559855, International Food Information Service Frankfurt-Main.
Guerard, F., et al, "Production of tuna waste hydrolysates by a commercial neutral protease preparation", 2002, Journal of Mol. catalysis B: Enzymatic 19-20: 489-498.

* cited by examiner

*Primary Examiner* — Hamid R Badr
(74) *Attorney, Agent, or Firm* — Norris McLaughlin & Marcus PA

(57) ABSTRACT

Provided is an enzymatic process that hydrolyzes spinach plant material to form a salt-enhancing ingredient, the formed salt-enhancing ingredient, food products comprising said salt-enhancing ingredient and a method of enhancing the salty taste of food products.

15 Claims, No Drawings

ENZYMATIC PROCESS

This is a continuation patent application of U.S. Ser. No. 12/996,731, which an application filed under 35 USC 371 of PCT/CH2009/000201, and which claims the priority benefit of U.S. Provisional patent application Ser. No. 61/074,167, the entirety of the contents of the foregoing patent applications being herein fully incorporated by reference.

TECHNICAL FIELD

Disclosed is a novel ingredient and the enzymatic process to form said ingredient to enhances saltiness in food products, in particular in food products with a low or reduced sodium content, to improve their taste.

BACKGROUND

A high amount of sodium intake is considered to be detrimental to health and therefore there is a desire to reduce the amount of sodium chloride (NaCl) in food products, without reducing the desired salty taste at the same time. The salty taste is very important to the perceived flavour intensity and profile, especially for savory food products.

There exists a need in the food industry to provide ingredients that enhance the salty taste of food products so that sodium/NaCl can be reduced.

Potassium Chloride (KCl) is used to replace other salts, particularly NaCl. If KCl is used in the desired concentration to reduce NaCl, an undesirable bitter and metallic taste is perceived by the consumer. Furthermore, certain individuals desire to avoid KCl because of health concerns. It would therefore be of interest to find a product that is able to enhance the salty taste of NaCl so that KCl can be partially or completely replaced.

Spinach or its hydrolysates have not been known for a salt-enhancing effect.

SUMMARY

Various aspects of the invention comprise the following:
(1) A process of forming a salt-enhancing ingredient comprising the steps of
 (i) forming an aqueous slurry of spinach plant material, and
 (ii) forming a hydrolysate of spinach plant material by subjecting it to an enzymatic hydrolysis using one or more proteolytic enzymes.
(2) The process as described under item (1), wherein the formed salt-enhancing ingredient is inactivated by heating.
(3) The process as described under any one of items (1) to (2) wherein the one or more proteolytic enzymes are selected from the group consisting of proteinase, peptidase, and glutaminase.
(4) The process as described under any one of items (1) to (3) wherein the one or more proteolytic enzymes comprise both proteinase and peptidase enzymes.
(5) The process as described under any one of items (1) to (4) wherein the one or more proteolytic enzymes comprise an enzyme preparation from *Aspergillus oryzae* (Umamizyme™) and the hydrolysis is performed at 40° C. to 60° C.
(6) The process as described under any one of items (1) to (5) wherein the hydrolysate is formed by subjecting the spinach plant material to an enzymatic hydrolysis using one or more carbohydrase enzymes in parallel or subsequent to enzymatic hydrolysis by the one or more proteolytic enzymes.
(7) The process as described under any one of items (1) to (6) wherein the hydrolysate is subjected to fermentation using a *Lactobacillus*.
(8) The process as described under item (7) wherein the *Lactobacillus* microorganism is selected from the group consisting of *L. plantarum, L. casei, L. brevis* and *L. helveticus*.
(9) The salt-enhancing ingredient formed by the process as described under any one of items (1) to (8).
(10) The salt-enhancing ingredient as described under item (9) which is concentrated at least 1.5 times by removing water.
(11) The salt-enhancing ingredient as described under any one of items (9) to (10) wherein the salt-enhancing ingredient is spray-dried.
(12) A flavor composition for food products comprising the salt-enhancing ingredient as described under any one of items (9) to (11) and one or more food-grade excipient.
(13) The flavor composition as described under item (12) wherein the concentration of the salt-enhancing ingredient of claim 9 is 0.25 to 400 ppm based on the use of the unconcentrated salt-enhancing ingredient. Useful concentrations for the salt-enhancing ingredient (unconcentrated) in flavor compositions or food products include 0.25 to 300 ppm, 0.25 to 200 ppm, 0.5 to 100 ppm, and 0.5 to 20 ppm.
(14) A food product comprising the salt-enhancing ingredient as described under any one of items (9) to (11).
(15) The food product as described under item (14) wherein the concentration of the salt-enhancin ingredient as described under any one of items (9) to (11) is 0.25 to 400 ppm based on the use of the unconcentrated salt-enhancing ingredient.
(16) The food product as described under any one of items (14) to (15) which is a reduced or low sodium food product.
(17) The food product as described under item (16) wherein the sodium chloride concentration is 0.15% (wt/wt) to 3% (wt/wt).
(18) The food product as described under item (16) wherein the sodium chloride concentration is 0.15% (wt/wt) to 1.5% (wt/wt).
(19) The reduced or low sodium food product as described under any one of items (16) to
(18) additionally comprising KCl, optionally in a concentration of 0.1% to 2% (wt/wt) KCl.
(20) A method of providing a food product enhanced in saltiness wherein the salt-enhancing ingredient as defined under any one of items (9) to (11) is admixed to a food product.
(21) The method as described under item (16) wherein the food product is a reduced or low sodium food product optionally containing KCl, optionally in a concentration of 0.1% to 2% (wt/wt) KCl.

DETAILED DESCRIPTION

Surprisingly, it has been found that when spinach is treated enzymatically with one or more proteolytic enzymes including, without limitation, the enzyme classes of protease, peptidase, and glutaminase, an ingredient can be formed that has an enhancing effect on the perception of salty taste in food products and exhibits a salty taste of higher intensity.

By salt-enhancing is meant the effect of an ingredient on the salty taste in food which is found more pronounced (stronger, enhanced) in its taste intensity and/or longer in its duration as analyzed by trained panellists sensitive to salty taste, when comparing food comprising an ingredient with a salt-enhancing effect to food without an added salt-enhancing ingredient.

The enhanced intensity of the perception of salty taste by the salt-enhancing ingredient can be increased by additionally using a carbohydrase enzyme, either in parallel or consecutively, in its formation.

To avoid off-tastes that may become noticeable in some food products when using higher concentrations of the salt-enhancing ingredient (a higher concentration may be, for example, about 50 ppm or more, about 100 ppm or more, about 200 ppm or more, or about 300 ppm or more), it is advantageous to include glutaminase in the enzymatic treatment.

The enhanced intensity of the perception of salty taste can be further increased by an optional fermentation step employing *Lactobacillus* bacteria, for example, *Lactobacillus plantarum*.

Spinach

"Spinach" as used herein refers to the green leaves and/or stalks of a flowering plant in the family of Amaranthaceae (formerly known as Chenopodiaceae), including Spinacia oleracea, and the closely related species *Beta vulgaris* (also known as chard, spinach beet, silverbeet or perpetual spinach); *Atriplex* spec., including *A. hortensis* (also known as orache, French spinach, or mountain spinach); and *Chenopodium* spec., including C. bonus-henricus and *C. album* (also known as Wild spinach, Fat hen, Good King Henry or Lincolnshire spinach).

Spinach includes three to four types, Savoy, Flat/Smooth leaf spinach, Semi-savoy, and Baby.

Savoy has dark green, crinkly and curly leaves. The Bloomsdale and the Tyee are popular savoy type varieties. Flat/smooth leaf spinach has broad smooth leaves that are easier to clean and is grown for canned, frozen or processed foods. Semi-savoy is a hybrid variety with slightly crinkled leaves. Semi-savoy includes Five Star, a widely grown variety. Baby is of the flat-leaf type and its leaves are usually no longer than three inches.

Examples of spinach varieties include, without limitation, America, Bloomsdale or Bloomsdale Long Standing, Dominant, Giant Winter, Horenso, Medania, Sigmaleaf, Space, Trinidad, Tyee (savoy type), Olympia, Melody, Winter Bloomsdale, Bordeaux, Koto, Lazio, Vienna, Marathon, Seven R, Baker, Cascade, Olympia, Polka, Rainier, Shasta, Wolter, Bossanova, Bolero, Coho, Ambassador, Rainier, Rhythm 9, Hybrid #7, Skookum, Bejo 1369, Splendor, Indian Summer, Avon, Correnta, Nordic IV, Savoy Supreme, Space, Spokane, Springfield, Steadfast, Unipak 12, Mazurka, Chinook II, Hybrid 424, St. Helens, Baker, Imperial Express and Imperial Star.

Enzymes

Exemplary useful enzyme classes include proteolytic enzymes that hydrolyze bonds in a protein, and optionally, a carbohydrase.

Proteolytic enzyme preparations usually contain proteinases, which hydrolyze proteins to form small peptides, and peptidases, which hydrolyze small proteins or peptides, usually to release amino acids from their terminal ends. Often proteinases and peptidases with both endopeptidase and exopeptidase activity are included in such preparations, to efficiently break down a protein both from within and from the ends of each protein and resulting peptide.

Useful proteolytic enzymes include, without limitation, an enzyme with one or more of the following activities: protease, peptidase, glutaminase (including, without limitation, L-glutamine-amido-hydrolase (EC 3.5.1.2)), endoprotease, serine endopeptidase, subtilisin peptidase (EC 3.4.21.62).

Other proteolytic enzymes are useful as well, and a great variety is known and available; some additional types and examples are given below.

Proteolytic enzymes (also called proteases, proteinases, or peptidases) are currently classified in six groups including serine protease, threonine protease, cysteine protease, aspartic acid protease, metalloprotease, and glutamic acid protease. Proteolytic enzymes can cut at the end of a protein (exopeptidases) or attack internal peptide bonds of a protein (endopeptidases). Exopeptidases include, without limitation, aminopeptidases, carboxypeptidases, and carboxypeptidase A. Endopeptidases include, without limitation, trypsin, chymotrypsin, pepsin, papain, and elastase.

Proteolytic enzymes (EC 3.4 and EC 3.5) are classified by an EC number (enzyme commission number), each class comprises various known enzymes of a certain reaction type.

EC 3.4 comprises enzymes acting on peptide bonds (peptidases/proteinases) and EC 3.5 comprises enzymes that act on carbon-nitrogen bonds other than peptide bonds.

Examples for EC 3.4 include, without limitation, the following: aminopeptidase (EC 3.4.11), dipeptidase (3.4.13), dipeptidyl-peptidase (3.4.14), peptidyl-dipeptidase (3.4.15), serine-carboxypeptidase (3.4.16), metallocarboxypeptidase (3.4.17), cysteine-carboxypeptidase (3.4.18), omegapeptidase (3.4.19), serine-endopeptidase (3.4.21), cysteine-endopeptidase (3.4.22), aspartate-endopeptidase (3.4.23), metalloendopeptidase (3.4.24), threonine-endopeptidase (3.4.25).

Examples for EC 3.5 include, without limitation, proteolytic enzymes that cleave in linear amides (3.5.1), for example, without limitation, glutaminase (EC 3.5.1.2).

Various proteolytic enzymes are commercially available; the following proteolytic enzymes are available from Sigma-Aldrich: Achromopeptidase, Aminopeptidase, Ancrod, Angiotensin Converting Enzyme, Bromelain, Calpain, Calpain I, Calpain II, Carboxypeptidase A, Carboxypeptidase B, Carboxypeptidase G, Carboxypeptidase P, Carboxypeptidase W, Carboxypeptidase Y, Caspase, Caspase 1, Caspase 2, Caspase 3, Caspase 4, Caspase 5, Caspase 6, Caspase 7, Caspase 8, Caspase 9, Caspase 10, Caspase 13, Cathepsin B, Cathepsin C, Cathepsin D, Cathepsin G, Cathepsin H, Cathepsin L, Chymopapain, Chymase, Chymotrypsin, a-Clostripain, Collagenase, Complement C1r, Complement C1s, Complement Factor D, Complement factor I, Cucumisin, Dipeptidyl Peptidase IV, Elastase, leukocyte, Elastase, pancreatic, Endoproteinase Arg-C, Endoproteinase Asp-N, Endoproteinase Glu-C, Endoproteinase Lys-C, Enterokinase, Factor Xa, Ficin, Furin, Granzyme A, Granzyme B, HIV Protease, IGase, Kallikrein tissue, Leucine Aminopeptidase (General), Leucine aminopeptidase, cytosol, Leucine aminopeptidase, microsomal, Matrix metalloprotease, Methionine Aminopeptidase, Neutrase, Papain, Pepsin, Plasmin, Prolidase, Pronase E, Prostate Specific Antigen, Protease, Alkalophilic from *Streptomyces griseus*, Protease from *Aspergillus*, Protease from *Aspergillus* saitoi, Protease from *Aspergillus sojae*, Protease (*B. licheniformis*) (Alkaline), Protease (*B. licheniformis*) (Alcalase), Protease from *Bacillus polymyxa*, Protease from *Bacillus* sp, Protease from *Bacillus* sp (Esperase), Protease from *Rhizopus* sp., Protease S, Proteasomes, Proteinase from *Aspergillus oryzae*, Proteinase 3, Proteinase A, Proteinase K, Protein C, Pyroglutamate aminopeptidase, Renin, Rennin, Streptokinase, Subtilisin, Thermolysin, Thrombin, Tissue Plasminogen Activator, Trypsin, Tryptase, Urokinase.

One or more of the proteolytic enzymes described herein can be combined with a carbohydrase to increase the salt impact of the formed salt-enhancing ingredient.

Useful enzyme combinations include, without limitation, combinations wherein at least one proteolytic enzyme is combined with at least one carbohydrase.

Useful carbohydrase enzymes to break down carbohydrate plant material include, without limitation, carbohydrases with one or more of the following activities: beta-glucanase (including, without limitation, 1,3-beta-glucan-gluco-hydrolase (EC 3.2.1.58)), beta-amylase, cellulase, hemicellulase, xylanase.

For example, the following combinations are non-limiting examples of useful enzymes:

| Protease/Peptidase/Glutaminase | Carbohydrase |
|---|---|
| Protease | beta-glucanase |
| Protease | beta-amylase |
| Protease | cellulase |
| Protease | hemicellulase |
| Protease | xylanase |
| Endoprotease | beta-glucanase |
| Endoprotease | beta-amylase |
| Endoprotease | cellulase |
| Endoprotease | hemicellulase |
| Endoprotease | xylanase |
| Peptidase | beta-glucanase |
| Peptidase | beta-amylase |
| Peptidase | cellulase |
| Peptidase | hemicellulase |
| Peptidase | xylanase |
| serine endopeptidase | beta-glucanase |
| serine endopeptidase | beta-amylase |
| serine endopeptidase | cellulase |
| serine endopeptidase | hemicellulase |
| serine endopeptidase | xylanase |
| L-glutamine-amido-hydrolase | beta-glucanase |
| L-glutamine-amido-hydrolase | beta-amylase |
| L-glutamine-amido-hydrolase | cellulase |
| L-glutamine-amido-hydrolase | hemicellulase |
| L-glutamine-amido-hydrolase | xylanase |
| subtilisin peptidase | beta-glucanase |
| subtilisin peptidase | beta-amylase |
| subtilisin peptidase | cellulase |
| subtilisin peptidase | hemicellulase |
| subtilisin peptidase | xylanase |

A useful combination is a 1,3-beta-glucan-gluco-hydrolase (EC 3.2.1.58) with protease selected from a serine endopeptidase, a peptidase/protease, or a subtilisin peptidase (EC 3.4.21.62).

As 1,3-beta-glucan-gluco-hydrolase, for example, without limitation, one or more of Ceremix™ (Novozymes, Bagsvaerd, Denmark) or Viscozyme™ (Novozymes, Bagsvaerd, Denmark) may be used.

As protease/peptidase/glutaminase, for example, without limitation, one or more of Alcalase™, a serine endopeptidase (Novozymes, Bagsvaerd, Denmark), Umamizyme™, a protease/peptidase (Amano, Nagoya, Japan), or Flavorpro 373™, a subtilisin peptidase (Biocatalysts, Cardiff, UK), may be used.

All enzymes used should be food-grade.

Enzymatic Hydrolysis

Enzymatic hydrolysis is performed under conditions suitable for all enzymes employed. As will be apparent to the skilled person, the temperature and pH should be within a suitable range for hydrolysis to occur to the desired degree. The incubation length will vary accordingly, with shorter incubations when conditions are nearer to the optimum conditions. Usually 1 to 48 hours will be sufficient, for example, 10 to 24 hours. Necessary ions, if required or beneficial for the chosen enzyme(s), should be present, as the skilled person will be aware. Stirring the incubation mix, for example 50 to 500 rpm, or 100 to 200 rpm, usually improves the hydrolysis. Some enzymes tolerate stirring better than others. Tolerance towards one factor often depends on the other factors. Such information on suitable conditions is readily available for many enzymes and otherwise can be easily determined.

A number of enzyme preparations, including Ceramix™, Alcalase™, Viscozyme™, and Umamizyme™, will work well in a liquified slurry of spinach in water at a temperature from 40° C. to 55° C., for example about 45° C. to about 55° C., without pH adjustment or any added co-factors. Others may need or will benefit from pH or temperature adjustment, or additives. Umamizyme™ will tolerate temperatures from about 40° C. to about 60° C., with an optimum at around 55° C. Umamizyme™ originates from *Aspergillus oryzae* and is rich in endopeptidase and exopeptidase activity.

Sufficient units of the enzyme to achieve a substantial hydrolysis until the desired degree of salty taste is achieved should be used.

The amount of enzyme is chosen to ensure sufficient activity and avoid developing bitter notes. The amount used depends on the activity of the enzyme, this information is usually known, else it can be tested easily. The amount of enzyme also depends on the amount of substrate (protein or carbohydrate) and there should be a ratio of 0.5:20 to 3:20 of enzyme:substrate (0.5 to 3 parts enzyme for 20 parts of substrate), for example 1:20 of enzyme:substrate (Ceremix™, Novozymes, Bagsvaerd, Denmark, has an activity of 300 Beta-Glucanase Units (BGU) per gram of enzyme; Viscozyme™, Novozymes, Bagsvaerd, Denmark, has an activity of 100 Fungal Beta-Glucanase Units FBG per gram of enzyme; Alcalase™, Novozymes, Bagsvaerd, Denmark, has an activity of 2.4 Anson untis (AU) per gram of enzyme; Umamizyme™, Amano, Nagoya, Japan, has an activity of 70 U (Units by LGG method, LGG=L-Leucyl-Glycyl-Glycine); Flavorpro 373™, a Glutaminase, Biocatalysts, Cardiff, UK, has an activity of 30 Glutaminase Units (GU)).

Useful amounts of enzyme units per gram starting material are indicated for some type of enzymes below.

Beta-Glucanase Units (BGU) per gram starting material (liquified spinach slurry) 0.03 to 15 BGU, for example 0.1 to 3 BGU.

Fungal Beta-Glucanase Units FBG per gram starting material, 0.002 to 3 FBG, for example, 0.01 to 1 FBG.

Anson untis (AU) per gram starting material, 0.0002 to 0.02 AU, for example 0.0005 to 0.01.

U (Units by LGG method, LGG=L-Leucyl-Glycyl-Glycine) per gram starting material 0.007 to 0.7 U, for example, 0.01 to 0.1 U are used.

Glutaminase Units (GU) per gram starting material, 0.00075 to 0.075 GU, for example, 0.001 to 0.02 GU are used.

The amount of enzyme will vary depending on enzyme and conditions it is used in. The necessary amount can be easily determined by trying out different amounts and testing the effect of the resulting product in a sensory evaluation as described herein.

The hydrolysate of the spinach slurry hydrolyzed by one or more of proteolytic and optionally one or more of carbohydrase enzymes may be used directly as a salt-enhancing ingredient. Usually it will be heat-inactivated before use by a final heat treatment (sterilization or pasteurization) high and long enough to inactivate enzymes and optionally microorganisms, as detailed hereinunder.

Alternatively, the hydrolysate is subjected to a fermentation.

Fermentation

Fermentation is performed with a *Lactobacillus* bacterium, for example, *Lactobacillus plantarum*. Other *Lactobacillus* species may also be useful, for example, *L. casei, L. brevis* and *L. helveticus* may also be useful.

An overnight culture of *Lactobacillus* may be used, or the hydrolysate may be directly inoculated from a *Lactobacillus* clone, and the fermentation performed for a slightly longer time accordingly.

The seed culture/overnight culture for the following fermentation may be prepared by methods well-known in the art. It may be grown overnight, for example 12 hours, at the appropriate temperature for the microorganism. 37° C. is a suitable temperature for *L. plantarum*. Any suitable medium may be selected, for example MRS broth (Difco, United States of America).

The inoculated material is fermented for several hours, for example, 5 hours to 48 hours, 10 hours to 30 hours, or 15 hours to 25 hours.

The fermentation with *Lactobacillus* is started using the hydrolysate as fermentation broth and adding a sufficient volume of an overnight seed culture at a pH of at least 5 or higher, for example a pH of 5 to 7. Fermentation is allowed to proceed until the pH has lowered to at least pH 5.5 or lower, for example pH 5.5 to pH 4.5.

The fermentation temperature is chosen to accommodate the microorganism. Useful temperature ranges for *Lactobacilli* and in particular *L. plantarum* include, for example, from about 20° C. to about 40° C., from about 30° C. to about 40° C., or from about 35 to about 40° C., with an optimum of about 36° C. to about 38° C. At a low temperature the growth rate will be low, at a high temperature the microorganism will be killed or reduced in numbers.

The fermentation container should be minimally stirred to ensure proper mixing but at the same time ensure that the bacteria can grow anaerobically (*Lactobacilli* are facultative anaerobic but usually grow faster under anaerobic conditions, aerotolerance may be manganese-dependent).

The fermented product can be used directly as a salt-enhancing ingredient, but usually will be followed by a final heat treatment (sterilization or pasteurization) high and long enough to inactivate enzymes and microorganisms.

Usually the hydrolyzed or the fermented product will be heat-inactivated before use, for example by heating from about 60° C. to about 121° C. or higher for sufficiently long to inactivate enzymes and bacteria (for example, without limitation, any pasteurization or sterilization method, which are well known in the art, for example, without limitation, about 70° C., about 90° C. or higher for 30 min. When heating above about 100° C., for example, about 121° C. for 30 min, heating has to be performed under pressure, usually about 12-15 psi).

The pH during fermentation should be from about pH 5 to about pH 7. If the pH is below 5, *Lactobacillus plantarum* will grow very slowly and usually not sufficiently. During fermentation the pH will lower to about pH 4 or lower, for example about pH 5 to about pH 3.5.

Afterwards, the pasteurized fermentation broth may be filtered to remove any larger particles and may be concentrated, for example by evaporation, including boiling at for example up to about 100° C.

Form of Use

The salt-enhancing ingredient may be used as such or in filtered and/or concentrated form. Alternatively, the concentrated salt-enhancing ingredient may be used as a paste or powder or spray-dried by methods well known in the art. For the spray-dried salt-enhancing ingredient, well known carriers and anti-caking agents may be added.

Optional filtering may be performed by any suitable filtering method, such methods are well known in the art, for example, by passing through a felt filter bag in a filter centrifuge. The filtered culture (supernatant containing the remaining smaller solids, minus the biomass that includes larger undigested proteins) can be concentrated, for example concentrated 2× by evaporation/boiling at 100° C. The resulting concentrate's solid content can be determined using a moisture analyser and can be spray-dried, for example, onto a suitable carrier. Many carriers are well known in the art, for example, without limitation, a potato maltodextrin carrier (for example, a ratio of about 1:1 solids of the 2× concentrate to carrier may be suitable). Optionally an anti-caking agent may be added, such agents are well known. A suitable anti-caking agent is, for example, tricalciumphosphate (TPC); about 0.5% (wt/wt) based on total weight of the 2× concentrate would be a suitable amount.

The final form of the salt-enhancing ingredient may be chosen according to methods well known in the art and will depend on the particular food application. For liquid foods, for example soups, the salt-enhancing ingredient can be used without further processing in its liquid form. For dry applications such as crackers, the spray-dried concentrated salt-enhancing ingredient can be used.

The salt-enhancing ingredient may be directly added to food products, or may be provided as part of a flavour composition for flavouring food products.

Flavour compositions contain the salt-enhancing ingredient and optionally one or more food grade excipient. Suitable excipients for flavour compositions are well known in the art and include, for example, without limitation, solvents (including water, alcohol, ethanol, oils, fats, vegetable oil, and miglyol), binders, diluents, disintegranting agents, lubricants, flavoring agents, coloring agents, preservatives, antioxidants, emulsifiers, stabilisers, flavor-enhancers, sweetening agents, anti-caking agents, and the like. Examples of such carriers or diluents for flavours may be found e.g. in "Perfume and Flavor Materials of Natural Origin," S. Arctander, Ed., Elizabeth, N.J., 1960; in "Perfume and Flavor Chemicals", S. Arctander, Ed., Vol. I & II, Allured Publishing Corporation, Carol Stream, USA, 1994; in "Flavourings", E. Ziegler and H. Ziegler (ed.), Wiley-VCH Weinheim, 1998, and "CTFA Cosmetic Ingredient Handbook", J. M. Nikitakis (ed.), 1st ed., The Cosmetic, Toiletry and Fragrance Association, Inc., Washington, 1988.

The flavour composition may contain additional flavour ingredients including flavour compounds, flavours from natural sources including botanical sources and including ingredients made by fermentation. The flavour composition may have any suitable form, for example liquid or solid, wet or dried, or in encapsulated form bound to or coated onto carriers/particles or as a powder.

If the salt-enhancing ingredient is added as an unconcentrated liquid, about 0.25 ppm (0.00025% wt/wt) to about 400 ppm (0.4% wt/wt) are usually enough in reduced or low sodium applications, for example, without limitation, in soups and topical food applications such as chips, crisps and snacks.

Notably, lower concentrations of the salt enhancer (for example, below 25 ppm, below 50 ppm, below 100 ppm, or below 200 ppm) were found to have a better salt-enhancing effect than higher concentrations, for example of about 300 ppm. However, depending on the food product, a higher concentration may be needed, for example at least 25 ppm, at least 50 ppm, at least 100 ppm, at least 200 ppm, or at least 300 ppm. In addition to a decreasing salt-enhancing effect, higher concentrations may introduce off-tastes that depending on the food product the salt-enhancing ingredient will be used in may be not acceptable to the consumer.

For most topical food applications, about 0.5 to about 50 ppm are usually sufficient.

When using a concentrate (for example by distillation) or a spray-dried salt-enhancing ingredient, the concentrations indicated need to be adjusted with an appropriate factor to take into account of the concentration change in the salt-enhancing ingredient.

Food Products

The term food product is used in a broad meaning to include any product placed into the oral cavity but not necessarily ingested, including, without limitation, food, beverages, nutraceuticals and dental care products including mouth wash.

Food products include cereal products, rice products, pasta products, ravioli, tapioca products, sago products, baker's products, biscuit products, pastry products, bread products, confectionery products, dessert products, gums, chewing gums, chocolates, ices, honey products, treacle products, yeast products, salt and spice products, savory products, mustard products, vinegar products, sauces (condiments), processed foods, cooked fruits and vegetable products, meat and meat products, meat analogues/substitutes, jellies, jams, fruit sauces, egg products, milk and dairy products, cheese products, butter and butter substitute products, milk substitute products, soy products, edible oils and fat products, medicaments, beverages, juices, fruit juices, vegetable juices, food extracts, plant extracts, meat extracts, condiments, nutraceuticals, gelatins, tablets, lozenges, drops, emulsions, elixirs, syrups, and combinations thereof.

Of particular interest are, without limitation, food products traditionally high in sodium salt with a reduced sodium salt concentration, including condiments and sauces (cold, warm, instant, preserved, sate, tomato, BBQ Sauce, Ketchup, mayonnaise and analogues, bechamel), gravy, chutney, salad dressings (shelf stable, refrigerated), batter mixes, vinegar, pizza, pasta, instant noodles, french fries, croutons, salty snacks (potato chips, crisps, nuts, tortilla-tostada, pretzels, cheese snacks, corn snacks, potato-snacks, ready-to-eat popcorn, microwaveable popcorn, caramel corn, pork rinds, nuts), crackers (Saltines, 'Ritz' type), "sandwich-type" cracker snacks, breakfast cereals, cheeses and cheese products including cheese analogues (reduced sodium cheese, pasteurized processed cheese (food, snacks & spreads), savoury spreads, cold pack cheese products, cheese sauce products), meats, aspic, cured meats (ham, bacon), luncheon/breakfast meats (hotdogs, cold cuts, sausage), soya-based products, tomato products, potato products, dry spice or seasoning compositions, liquid spice or seasoning compositions including pesto, marinades, and soup-type/meal-alternative beverages, and vegetable juices including tomato juice, carrot juice, mixed vegetable juices and other vegetable juices.

Processed foods include margarine, peanut butter, soup (clear, canned, cream, instant, UHT), gravy, canned juices, canned vegetable juice, canned tomato juice, canned fruit juice, canned juice drinks, canned vegetables, pasta sauces, frozen entrees, frozen dinners, frozen hand-held entrees, dry packaged dinners (macaroni & cheese, dry dinners-add meat, dry salad/side dish mixes, dry dinners-with meat).

Soups may be in different forms including condensed wet, ready-to-serve, ramen, dry, and bouillon, processed and pre-prepared low-sodium foods.

Depending on the food product, for food products that contain about 10 to 100%, for example 25 to 50%, less sodium than a comparable food product (for example "reduced sodium" products with 25% reduction, or "light in sodium" products with a 50% reduction), the salt-enhancing ingredient may be employed as follows: a useful concentration for most food applications may be, for example, about 0.001% to about 0.015% (wt/wt) based on the unconcentrated salt-enhancing ingredient. Alternatively, for example, 25 to 300 ppm or 0.002% to 0.03% (wt/wt) based on a spray-dried 2× concentrate may be used.

The salt enhancer may be used in unconcentrated or concentrated form or the concentrate may be formulated into a paste or powder by methods known in the art. In this case the amount to be used has to be adjusted accordingly. Flavour compositions such as spices are often more concentrated, for example a 10× concentrate, and the concentration will be adjusted higher accordingly.

The NaCl concentration in common food products with a regular NaCl concentration varies with most products ranging from about 0.5% to about 5% (wt/wt) NaCl. Seasoning or products used as seasoning, such as croutons, sauces or salad dressings that are employed in a small amount (to be applied to, for example, salad or noodles), have a concentration of for example from about 2% to about 5% (wt/wt) NaCl. Soups usually contain about 0.6% to about 1.25% (wt/wt) NaCl. Salty crackers and meat products (salami, ham, bacon) usually contain about 2% to about 4% (wt/wt) NaCl. Cereals usually contain about 0.6 to 3% (wt/wt) NaCl. Products that need to be reconstituted (dry soups) usually range in the concentration ranges indicated after reconstitution.

For low sodium products containing even less NaCl than products with reduced sodium content (353 mg per serving), the amount of the salt-enhancing ingredient may have to be increased.

For food products with added KCl, depending on the food product and said ingredients, the concentration of KCl may be from about 0.1% or about 0.2% up to about 1%, up to about 1.5%, up to about 2% (wt/wt), or higher, depending on how much the sodium concentration is reduced. A KCl concentration of about 0.25% to about 1.5% (wt/wt), for example about 0.5% to about 1.5% (wt/wt) KCl will be useful for most low sodium products. A range to which the NaCl concentration may usefully be reduced for most applications is, for example, about 0.25% (wt/wt) to about 2.5% (wt/wt), or from about 0.125% to about 1.25% (wt/wt). The amount of the salt-enhancing ingredient to be added to the food product as an ingredient will depend on the concentration of KCl used, and the specific food product including the particular base and flavour. A useful concentration for most food applications may be, for example, about 0.001% to about 0.015% (wt/wt) based on the unconcentrated salt-enhancing ingredient. Alternatively, for example, 25 to 300 ppm or 0.002% to 0.03% (wt/wt) based on a spray-dried 2× concentrate may be used.

The salt-enhancing ingredient may be used in un-concentrated form or the concentrate may be formulated into a paste or powder or spray-dried salt-enhancing ingredient by methods known in the art. In this case, the amount to be used has to be adjusted accordingly.

The appropriate concentration of the salt-enhancing ingredient can be easily tested by an organoleptic titration. This technique is well known in the field of sensory analysis.

EXAMPLES

Unless otherwise indicated, percentages or ratios are given as wt/wt.

EXAMPLE 1

Enzymatic hydrolysis of spinach and fermentation of the spinach hydrolysate

Various different samples were prepared as indicated in the table below.

Fresh spinach leaves were finely chopped with a food processor. Water was added to the chopped spinach in a 1:9 ratio (water:spinach) and the slurry was liquified in the food processor.

A part of the liquified spinach slurry was separated by distillation into a volatile and a non-volatile/pot residue fraction.

In parallel, instead of liquified slurry of fresh spinach, liquified slurry of dehydrated (air dried) spinach powder was used in a concentration of 15% in water, and achieved similar results.

The liquified slurry of fresh or dehydrated spinach, or their non-volatile fractions, were heated to 50° C. and the following samples were prepared by adding the following digestive enzymes in the indicated concentrations (w/w) to the slurry:

a) Viscozyme™ (0.1%) and Umamizyme™ (0.1%) UV
b) Umamizyme™ (0.1%), Viscozyme™ (0.1%) and Glutaminase Flavorpro 373™ (0.025%) UVG

| Spinach leaves slurry samples | Enzymes |
|---|---|
| Fresh - total - control | — |
| Fresh - total a) | U&V |
| Fresh - total b) | UV&G |
| Fresh - volatiles - control | — |
| Fresh - non-volatiles - control | — |
| Fresh - non-volatiles a) | U&V |
| Fresh - non-volatiles b) | UV&G |
| Powder - control | — |
| Powder - total a) | U&V |
| Powder - total b) | UV&G |
| Powder - volatiles - control | — |
| Powder - non-volatiles - control | — |
| Powder - non-volatiles a) | U&V |
| Powder - non-volatiles b) | UV&G |

Viscozyme™ (Novozymes, Bagsvaerd, Denmark) has an activity of 100 Fungal Beta-Glucanase Units FBG per gram of enzyme; per gram starting material, 0.1 FBG are used. Umamizyme™ (Amano, Nagoya, Japan) has an activity of 70 U (Units by LGG method, LGG=L-Leucyl-Glycyl-Glycine); per gram starting material, 0.07 U are used.

A Glutaminase, Flavorpro 373™ (Biocatalysts, Cardiff, UK), may be used as a proteolytic enzyme. Flavorpro 373™ has an activity of 30 Glutaminase Units (GU); per gram starting material, 0.0075 GU are used.

Enzymatic hydrolysis was allowed to proceed for 20 to 24 hours at 50° C. while stirring at 150 rpm to form a hydrolysate.

The hydrolysate was then cooled to 37° C. and inoculated with an overnight culture of a strain of *Lactobacillus plantarum* (cell density of about $10^6$ cells/g) in a concentration of 0.3% overnight culture per hydrolyzed material/fermentation broth.

The inoculated material underwent fermentation for about 24 hours (or until the pH had lowered to about pH 4) at 37° C. under minimal stifling. Fermentation was followed by a final heat treatment of 121° C. for 30 min.

EXAMPLE 2

Sensory Evaluation

The samples of example 1 were organoleptically evaluated by trained flavorists in a 50% sodium-reduced, fat-free chicken broth (sodium 480 mg/serving) in two sample or control concentrations (5 ppm and 300 ppm). The chicken broth was served warm (about 37° C.) for tasting and all samples were presented blinded (so their identity cannot be identified by panelists).

Each of the samples was compared to a control processed as described in example but without the enzyme treatment, and an increased salt taste intensity over the control was rated as follows: + slightly salty, ++ salty, +++ strong salty taste.

The results are shown in the table below.

| Spinach leaves slurry samples | Enzymes | Enhancement of saltiness 300 ppm | Enhancement of saltiness 5 ppm |
|---|---|---|---|
| Fresh - total - control | — | − | − |
| Fresh - total a) | U&V | ++ | +++ |
| Fresh - total b) | UV&G | ++ | +++ |
| Fresh - volatiles - control | — | − | − |
| Fresh - non-volatiles - control | — | − | − |
| Fresh - non-volatiles a) | U&V | ++ | +++ |
| Fresh - non-volatiles b) | UV&G | ++ | +++ |
| Powder - control | — | − | − |
| Powder - total a) | U&V | ++ | +++ |
| Powder - total b) | UV&G | ++ | +++ |
| Powder - volatiles - control | — | − | − |
| Powder - non-volatiles - control | — | − | − |
| Powder - non-volatiles a) | U&V | ++ | +++ |
| Powder - non-volatiles b) | UV&G | ++ | +++ |

Salt Enhancement when Compared to Controls without Enzyme Treatment

All panelists found that the cultured hydrolyzate of the fresh spinach leaves sample, as well as that of dry spinach powder, showed a good salt-enhancing effect at a concentration of 5 ppm resulting in a pleasantly upfront salty taste very similar in its temporal flavor profile to sodium chloride, without any off-taste. The effect was decreased somewhat in the samples containing 300 ppm, and, a slight metallic off-taste (++) was noted by some panelists, especially in the powder-nonvolatiles a) sample with UV but without G. The other samples treated with U and V but not G also had a very slight off-taste (+), compare results in the table below.

| Spinach leaves slurry samples | Enzymes | Off-taste 5 ppm | Off-taste 300 ppm |
|---|---|---|---|
| Fresh - total a) | U&V | − | + |
| Fresh - total b) | UV&G | − | − |
| Fresh - non-volatiles a) | U&V | − | ++ |
| Fresh - non-volatiles b) | UV&G | − | − |
| Powder - total a) | U&V | − | + |
| Powder - total b) | UV&G | − | − |
| Powder - non-volatiles a) | U&V | − | + |
| Powder - non-volatiles b) | UV&G | − | − |

Comparison UV & UVG, presence of off-tastes

EXAMPLE 3

Sensory Evaluation

The evaluation was performed as essentially as described in example 2 leaving out the carbohydrate enzyme (sample without "V"). When compared to samples with V carbohydrate enzyme, the increase in saltiness was found to be less pronounced.

While the processes, ingredients and food products have been described above in connection with certain illustrative embodiments, it is to be understood that other similar embodiments may be used or modifications and additions may be made to the described embodiments for performing the same function(s). Further, all embodiments disclosed are not necessarily in the alternative, as various embodiments may be combined to provide the desired characteristics. Variations can be made by one having ordinary skill in the art without departing from the scope of the disclosure. Therefore, the processes, ingredients and food products should not be limited to any single embodiment, but rather construed in breadth and scope in accordance with the recitation of the attached claims.

The invention claimed is:

1. A process of producing a salt-enhancing ingredient comprising the steps of:
   (i) forming an aqueous slurry of spinach plant material,
   (ii) forming a hydrolysate of spinach plant material by subjecting it to an enzymatic hydrolysis using one or more carbohydrase enzymes in parallel or subsequent to enzymatic hydrolysis by one or more proteolytic enzymes, and,
   (iii) fermenting the hydrolysate of the spinach plant material at a temperature from about 20° C. to about 40° C. by using *L. plantarum*.

2. The process of claim 1, wherein the one or more enzymes and the *Lactobacillus plantarum* bacterium in the formed salt-enhancing ingredient is inactivated by heating.

3. The process according to claim 1, wherein the one or more proteolytic enzymes are selected from the group consisting of proteinase, peptidase, and glutaminase.

4. The process according to claim 1, wherein the one or more proteolytic enzymes comprise both endopeptidase and exopeptidase activity.

5. The process according to claim 1, wherein the one or more proteolytic enzymes comprise an enzyme preparation from *Aspergillus oryzae* and the hydrolysis is performed at 40° C. to 60° C.

6. The salt-enhancing ingredient produced by the process of claim 1.

7. The salt-enhancing ingredient according to 1 which is concentrated at least 1.5 times by removing water.

8. The salt-enhancing ingredient according to claim 6, wherein the salt-enhancing ingredient is spray-dried.

9. A flavor composition for food products comprising the salt-enhancing ingredient according to claim 6 and one or more food grade excipients.

10. The flavor composition according to claim 9 wherein the concentration of the salt-enhancing ingredient is 0.25 to 400 ppm.

11. A food product comprising the salt-enhancing ingredient according to claim 6, which is present at a concentration of 0.25 to 400 ppm.

12. The food product of claim 11 which is a reduced or low sodium food product having a sodium chloride concentration is 0.15% (wt/wt) to 3% (wt/wt).

13. The reduced or low sodium food product according to claim 12, additionally comprising potassium chloride.

14. A method of producing a food product enhanced in saltiness the method comprising the step of: admixing to a food product a salt-enhancing ingredient according to claim 6.

15. The method of claim 14 wherein the food product is a reduced or low sodium food product.

* * * * *